(12) United States Patent
Taylor et al.

(10) Patent No.: US 7,625,087 B2
(45) Date of Patent: Dec. 1, 2009

(54) PUPILLOMETERS

(75) Inventors: Daniel Robert Stafford Taylor, Christchurch (GB); Alan Thomas Cayless, Stirling (GB)

(73) Assignee: Procyon Instruments Limited, London (GB)

( * ) Notice: Subject to any disclaimer, the term of this patent is extended or adjusted under 35 U.S.C. 154(b) by 56 days.

(21) Appl. No.: 11/663,701

(22) PCT Filed: Sep. 23, 2005

(86) PCT No.: PCT/GB2005/003696

§ 371 (c)(1),
(2), (4) Date: Oct. 19, 2007

(87) PCT Pub. No.: WO2006/032920

PCT Pub. Date: Mar. 30, 2006

(65) Prior Publication Data

US 2008/0198330 A1    Aug. 21, 2008

(30) Foreign Application Priority Data

Sep. 23, 2004    (GB) .................................. 0421215.5

(51) Int. Cl.
*A61B 3/10* (2006.01)
*A61B 3/02* (2006.01)
(52) U.S. Cl. ........................ 351/205; 351/210; 351/221; 351/237
(58) Field of Classification Search ................ 351/204, 351/205, 209, 210, 211, 221, 222, 237, 246
See application file for complete search history.

(56) References Cited

U.S. PATENT DOCUMENTS

| | | | |
|---|---|---|---|
| 5,784,145 A * | 7/1998 | Ghodse et al. | 351/205 |
| 6,217,172 B1 | 4/2001 | Shibutani et al. | |
| 2004/0041980 A1 | 3/2004 | Laguette et al. | |
| 2006/0017883 A1 * | 1/2006 | Dai et al. | 351/205 |

FOREIGN PATENT DOCUMENTS

| | | |
|---|---|---|
| EP | 1302153 | 4/2003 |
| WO | 94/07406 | 4/1994 |

OTHER PUBLICATIONS

International Search Report with Written Opinion for PCT/GB2005/003696 of Dec. 8, 2005.

* cited by examiner

*Primary Examiner*—Huy K Mai
(74) *Attorney, Agent, or Firm*—Hueschen and Sage (57) ABSTRACT

Pupillometric apparatus for assessing pupillary near reflex in a subject incorporates a visible fixation point which is moveable between near and far positions and which is viewable through an eyepiece via an accomodation lens positioned between the eyepiece and the near position. The focal length of the accomodation lens exceeds the distance of the lens from both the near and far positions of the fixation point, so that the subject always observes virtual images in respect of the fixation point. In this way the distance between observed virtual positions of the fixation point at its near and far positions exceeds the actual distance between these positions.

Binocular pupillometric apparatus in which images of the left and right pupils of a subject are rapidly and alternately transmitted to the same part of a single image sensor and signal data so obtained are processed to generate separated image data representative of the dimensions of the left and right pupils is also disclosed.

24 Claims, 7 Drawing Sheets

PUPILLOMETERS

This invention relates to pupillometers, i.e. to apparatus for determining pupil dimensions in respect of the eyes of a subject, generally (although not necessarily exclusively) a human subject. More particularly the invention concerns apparatus which permits assessment of pupillary near-reflex, either monocularly or binocularly. Another embodiment concerns binocular apparatus capable of substantially simultaneously determining pupil dimensions in respect of the left and right eyes using a single optical sensor.

Pupillometers have a wide variety of medical applications. Thus, for example, the dimensions of the pupil are important in corneal surgery, since the size of the optical zone (i.e. the light-admitting element of the eye which is surgically altered) must not be smaller than the maximum size of the pupil in any patient.

Measurement of a subject's pupillary response to light stimuli may be used to determine the state of the subject's autonomic nervous system, e.g. to detect fatigue or the presence of drugs, or as an early indicator of disease of the retina or optic tract (C. Ellis, Journal of Neurology, Neurosurgery and Psychiatry 42, pp. 1008-1017 [1979]).

Measurement of anisocoria (inequality of pupil sizes) plays an important role as a diagnostic test for disease, since subjects with corneal abrasions, marginal keratitis and acute anterior uveitis have significantly smaller mean pupillary diameters in the affected eye. Other applications for anisocoria measurements include the diagnosis and localisation of lesions in Homer's syndrome, the detection of neuro-ophthalmic and ophthalmic disease in newborn infants and in subjects exhibiting Pigmentary Dispersion Syndrome, and the detection of physiological effects of opiate abuse, e.g. using the naloxone eyedrop test described by Creighton et al. in The Lancet (Apr. 8, 1989), pp. 748-750.

Existing pupillometers typically project an image of the eye, usually generated by infrared irradiation, by way of a lens assembly onto an optical detector, e.g. a photographic film or an electronic sensor such as a two-dimensional charge-coupled device (CCD) array. U.S. Pat. No. 6,022,109 lists a body of prior art relating to pupillometers and their use, and itself describes a self-contained hand-held pupillometer capable of monocular operation.

Another pupillometer operating in an essentially monocular manner is described in U.S. Pat. No. 5,661,538. Thus, although provided with binocular eyepieces, this pupillometer uses a rotatable mirror to select which eyepiece communicates optically with a semi-passive optical target, so that images of only one eye at a time are investigated.

Monocular operation is fundamentally unsatisfactory for anisocoria measurements, since although background illumination etc. may be standardized, it is not possible to control the effects of the higher centres of the brain; pupil sizes may therefore vary significantly with time. Hippus (pupillary unrest) is also always present; the amplitude of oscillations which may occur is thought to be influenced by factors such as respiratory function and fatigue. Separate measurements of the pupils at different times therefore cannot provide accurate anisocoria measurements.

This is particularly the case in the above-mentioned naloxone eyedrop test, in which a naloxone eyedrop is administered to one eye of a subject and pupil size is measured after a period of time relative to the untreated eye; a mydriatic response is generally observed in the test eye of opiate addicts. In order to obtain consistent results in this test it is in practice necessary to determine pupil dimensions in respect of both eyes within about 0.2 seconds of each other, since pupil response time is of this order of magnitude. Otherwise anomalies may occur, for example as a result of changes in ambient illumination or random thoughts on the part of the subject.

Typical binocular pupillometers comprise two separate image sensors, e.g. two video cameras mounted on individual stands, and require the subject to be seated with his or her head resting on a chin rest or head clamp. Such systems and the necessary accompanying electronic circuitry inevitably require considerable space; a dedicated laboratory with controlled levels of illumination and accommodation is generally a prerequisite. The use of binocular apparatus of this type (the Applied Science Laboratories Series 1050 TV Pupillometer) in the diagnosis of Alzheimer's disease is disclosed in U.S. Pat. No. 6,162,186.

U.S. Pat. Nos. 5,042,937 and 5,210,554 both describe a system in which both pupils may be imaged using a single sensor. Here bright pupil images (i.e. "red eye" images) of the two pupils are projected onto separate areas of a CCD sensor. In order to obtain these bright pupil images it is necessary to illuminate the eyes along the same axes which are used for imaging so as to achieve direct reflection of the illumination from the retina of each eye. Accordingly very careful positioning of the optics relative to the eyes of the subject is required. The instrumentation is therefore bulky and complex.

A more compact and mechanically far less complex binocular pupillometer which permits imaging using a single sensor is described in WO-A-9407406. In this apparatus, which may be in portable form, images of both pupils are simultaneously transmitted along separate optical paths to separate areas of a common optical sensing means. Divider means are positioned close to the optical sensing means and between the two optical paths, in order to enhance optical separation between the two detection areas and the optical paths leading thereto. In this way cross-talk artefacts are prevented from interfering with the image analysis.

An alternative approach to the use of scanning devices such as CCDs is to measure the output power of incident infrared light which has been reflected by the retina back through the pupil, for example as described in U.S. Pat. No. 6,199,985. Such measurements may be used to provide information on relative pupillary size changes in response to visible light stimulation, but the apparatus additionally requires a calibration channel to compensate for factors such as differences in the pupil to retina distances for individual subjects in order to convert the relative data to a nominally more absolute form. This need separately to calibrate the apparatus to each patient represents a disadvantageous complication of such systems.

The present invention is in part based on the finding that binocular pupil measurements may be made in an effective manner using a pupillometer with a particularly simple optical system in which alternating images of the two eyes of a subject are successively transmitted to the same part of a single image sensor. The alternating images are generated by alternately illuminating the eyes at an appropriate frequency; the resulting interleaved signals from the sensor in respect of the left and right eyes may be processed to provide separate image data in respect of the left and right pupils.

Thus according to one aspect of the present invention there is provided binocular apparatus for substantially simultaneous determination of pupil dimensions in respect of the left and right eyes of a subject, said apparatus comprising (i) left and right eyepieces for positioning against the eyes, (ii) sensing illumination means whereby in use the left and right eyes are independently and alternately illuminated via the eyepieces to generate alternating images defining the left and right pupils, (iii) an optical train whereby in use said alternating left and right pupil images are transmitted to the same part of a single image sensor, and (iv) signal processing means associated with said sensor and adapted to separate signals generated therein by said alternating images and to generate separated image data representative of the dimensions of the left and right pupils.

In accordance with a further aspect of the invention there is provided a method for substantially simultaneous determination of pupil dimensions in respect of the left and right eyes of a subject, said method comprising alternately illuminating the left and right eyes in order to generate alternating images defining the left and right pupils, projecting said alternating left and right pupil images onto the same part of a single image sensor, separating signals generated by said sensor in respect of left pupil images and right pupil images, and generating separated image data representative of the dimensions of the left and right pupils.

The image sensor is preferably a CCD array or other scanning sensor. As is well known, the video output from such sensors produces field synchronization pulses every field, each field being scanned by the scanning circuitry as a series of adjacent lines. In many existing usages alternate fields scan alternate lines, the two fields then being combined ("interlaced") to provide a complete picture with enhanced spacial resolution.

In embodiments of the present invention, however, each separate field is digitized and digitized images representing the left and right pupils are stored in separate buffers. An appropriate computer programme may then be run to analyze the image data and calculate the respective pupil sizes. The resulting spatial resolution is wholly adequate for the purposes of pupil measurements.

Digitisation may, for example, be performed using a PCM-CIA frame capture card in conjunction with a laptop computer for capture rates of up to five 540 by 390 pixel frames per second, or using a frame grabber card connected via the ISA bus of a desktop personal computer for capture rates of up to 25 frames per second. Given that, as noted above, the response time of the pupils is typically in excess of 0.2 seconds, both of these methods generate what are essentially simultaneous images defining the left and right pupils, since the delay between recordal of left and right pupil image data is insignificant in comparison with the biological time constants of the pupillary system. Results obtained in accordance with the invention are therefore in practice comparable to results obtained using truly simultaneous pupil measurements, but are achieved using simpler and therefore cheaper apparatus. Errors caused by any short term pupillary motion and unrest may be avoided by averaging out the results obtained in respect of each eye over a period of several (e.g. 1-5, 1-3 or 1-2) seconds.

In a preferred embodiment of the invention the sensing illumination means comprise infrared-emitting diodes which are associated with each eyepiece so that the eyes may be independently and alternately illuminated. Such diodes may be synchronized to the field scan rate of the image sensor in order to permit ready separation of the alternating left and right pupil image data generated by the sensor.

Where infrared illumination is used in this way, it will be scattered back from the iris and may be transmitted through a suitable optical train (e.g. as described hereinafter) to form an image of at least the internal boundary of the iris with the pupil. In some embodiments (e.g. as hereinafter described in relation to cataract surgery) it may also be useful to record image data in respect of the outer boundary of the iris with the sclera. Processing of the image data in respect of either or both of these boundaries may, for example, be performed using techniques such as image enhancement, automatic measurement of pupil area and/or maximum and minimum dimensions, and/or application of a circle fitting algorithm, e.g. so as to detect variations from absolute circularity in pupil shape. Representative embodiments of such techniques are illustrated in further detail in the aforementioned WO-A-9407406, the contents of which are incorporated herein by reference.

The synchronization pulses from the image sensor may be used to trigger simple logic circuitry, e.g. a bistable flip flop, in order to activate such infrared-emitting diodes alternately during successive scans. The operating sequence is advantageously designed always to begin with the same (i.e. left or right) eye so that the identity of the pupil in each image is unambiguously determined.

The eyepieces may advantageously be periscopic in form, for example as described in the aforementioned WO-A-9407406, so as to permit ready adjustment for subjects with different interpupillary distances without altering the overall optical path length of the apparatus.

If desired the apparatus may additionally incorporate background illumination means, e.g. comprising one or more light-emitting diodes, whereby the eyes may be illuminated via the eyepieces. In some preferred embodiments each eye may be illuminated with an independently controllable amount of visible light. This permits the measurement of pupil diameters under a range of conditions, for example over time at constant ambient illumination or in response to applied light or darkness stimuli (this last being achieved by switching off previous ambient illumination).

One application of such embodiments of pupillometers according to the invention is in the measurement of relative afferent pupillary defect, a condition wherein nerve signals from the eye to the brain are unilaterally compromised, for example by retinal lesions or by damage to the optic nerve. In healthy subjects the left and right pupils react bilaterally to a light stimulus, both pupils contracting when a light stimulus is applied to one eye only, and contracting by the same amounts when the same stimulus is applied to the other eye. When relative afferent pupillary defect is present, however, both pupils still contract in response to a unilateral stimulus, but this bilateral contraction is smaller when the light stimulus is presented to the eye on the affected side.

As noted earlier (Ellis, op. cit.), the use of pupillometry to determine the severity of retinal and optical tract disease is well established. The amplitude of the pupil-light reflex and the peak velocity of constriction may easily be measured from pupillary motion data output in response to alternately stimulating the left and right eyes with white light, the affected eye exhibiting smaller pupillary reactions than the unaffected eye. Simultaneous measurement of both eyes using a binocular pupillometer confirms this more powerfully and conclusively than does separate measurement of each eye.

Currently the usual clinical procedure for diagnosis of relative afferent pupillary defect is the "swinging flashlight test", which employs a small handheld flashlight which is shone into each eye alternately for one or two seconds, the clinician judging whether there is any inequality in the magnitude of the pupillary reactions. A set of small neutral density filters may then be used to estimate the magnitude of any observed defect, the flashlight being occluded with such a filter when shone into the healthy eye, with the magnitude of the filter being adjusted until the two pupils respond equally. The magnitude of the filter is then used as an index of the magnitude of the afferent pupillary defect.

Whilst this existing precedure is simple and quick to carry out, it suffers the disadvantage of subjectivity. Thus repeatability will be questionable and some interoperative variation must occur since stimulus intensity and duration are neither precisely controlled nor controllable. Moreover, since the method inherently requires attenuation of stimulus to the eye with the larger response, the final measurement will necessarily be made at a relatively low response level, resulting in a loss of resolution and an escalation of measurement errors.

A similar but more objective result may be achieved in accordance with the invention by including a negative feedback control loop to calculate any difference between healthy and unhealthy eye responses and using this difference to modify the visible light stimuli until the two pupillary responses are equal.

A more robust method, however, involves presentation of light stimulus pulses of precise duration and intensity to each eye in turn; pulse durations of 200 ms may conveniently be employed, although both longer and shorter pulses may also be used, e.g. with durations in the range 100-500 ms. The pupillometer is used to measure the pupillary responses to each light pulse, for example in terms of one or more parameters such as latency period between onset of stimulus and onset of constriction, depth of constriction, maximum speed of constriction, average speed of constriction, redilation time, and time to reach a specific degree (e.g. 25%, 50% or 75%) of constriction and/or redilation. The stimulus pulses are preferably unilaterally presented to each eye at four or more intensity levels, with each stimulus level optionally being repeated one or more times. The average value of the chosen response parameters for each stimulation level to each eye is then plotted (e.g. graphically or digitally) against the intensity of that level to give a pupillary response profile.

As discussed in further detail hereinafter, the response profiles for stimulation of the left and right eyes of healthy subjects will substantially completely overlap. For subjects with relative afferent pupillary defect, on the other hand, stimulation of one eye will generate a consistently lower response than does stimulation of the other eye. The extent of the disorder can be quantified by determining the shift between the two profiles along the direction of the stimulus intensity axis, since this represents the light intensity scaling factor required to bring the two profiles into coincidence, and so is an equivalent of the neutral density filter magnitude obtained in the swinging flashlight test.

Particular advantages of this procedure are that it provides a single repeatable process which may use a set sequence of convenient and desirably standardized stimulus intensities and durations. There is no iteration or judgment as to when two responses are equal, and measurements may be made over a substantial range of stimulus intensities (e.g. covering three or more decades) while giving equal weight to all the data collected.

It will be appreciated that the above procedure may be used to generate any or all of four classes of pupil response profile, viz. response of the right pupil when the right eye is stimulated, response of the right pupil when the left eye is stimulated, response of the left pupil when the right eye is stimulated, and response of the left pupil when the left eye is stimulated. Pupillometers in accordance with the invention may therefore also be used in the diagnosis of conditions wherein the left and right pupils contract differently in response to a single unilateral stimulus, for example in the measurement of efferent defects. Symptoms such as Horner's syndrome, in which one pupil is much smaller than the other and responds less well to changes in illumination, are usually confirmed according to current clinical practice by using cocaine eyedrops. This is because there are several other similar conditions (e.g. such as Adie's tonic pupil) which have different causes. In Horner's syndrome the cause is a lesion in the sympathetic nerves exiting the spinal cord, this resulting in innervation of organs on one side of the body. The dilator muscle of the iris is controlled by such sympathectic nerves, and if the signals are interrupted this muscle becomes less active. The pupil is usually noticeably smaller on the affected side, and does not react to darkness by rapid dilation in the usual way, increasing in size more slowly than the healthy eye.

As noted above, a test involving the topical application of cocaine eyedrops is currently used to confirm the diagnosis of Homer's syndrome. Cocaine is a sympathetico-mimetic drug which stimulates sympathetic nerve receptors in the iris muscle. If the iris responds well to cocaine eyedrops applied to the conjunctival sac, with the pupil dramatically increasing in size, the conclusion is that the efferent pathway is affected so that follow up investigation should ensue.

A similar diagnosis may, however, be performed using a pupillometer in accordance with the invention to examine the pupillar response to darkness. Both eyes are suddenly exposed to a darkness stimulus by switching the illuminating light-emitting diodes off together, while at the same time monitoring the pupils. It can quickly and objectively be deduced from the resulting pupillary responses whether there is a significant difference in pupil size before the darkness stimulus and whether the pupils respond at different rates to this stimulus. The need for cocaine eyedrops is obviated since the data provide objective evidence of the symptoms.

Another useful application of pupillometers according to the invention is in determining patient suitability for refractive surgery. The American Society of Cataract and Refractive Surgeons recommends measurement of pupil size in dim illumination for all candidates contemplating laser in situ keratomileusis treatment. The term "dim illumination" is, however, inherently ambiguous. The International Commission on Illumination (CIE) have the following definitions: scotopic illumination, in which only retinal rods are active, is anything less than 0.05 lux; mesopic illumination, in which both retinal rods and cones are active to some degree, is between 0.05 and 50 lux; and photopic illumination, in which only retinal cones are active, is greater than 50 lux. Pupillometers of the present invention may be used to measure the pupil under a range of precisely defined (e.g. low) illumination levels which may be based on these standard definitions. By taking an average of data dynamically acquired over a period of several seconds such pupillometers are unaffected by the inevitable small oscillatory movements of the pupil and so provide greater accuracy and repeatability than single measurement devices.

In cataract surgery the size of the external boundary of the iris is important in estimating the size of the anterior chamber, which is used in determining the characteristics of any intraocular lens which is fitted. Thus it is important to ensure that the patient's pupil size in dim illumination is no larger than the diameter of the intraocular lens. Pupillometers according to the invention may be used to measure the external diameter of the iris using a circle fitting process which requires no more than one or two images containing some iris-sclera edge information. Once the centre of the pupil has been found the iris edges can be sought since they will always be within a certain radius of this centre.

Pupillometers of the invention may also be used in the accurate determination of any change in anisocoria resulting from topical application of a pharmaceutical eyedrop, for example as in the above-described naloxone eyedrop test. It will be appreciated that, since most individuals exhibit natural anisocoria as well as pupillary unrest, the substantially simultaneous binocular measurement of pupil sizes in accordance with the invention, followed by averaging of each pair of observed size differences, will provide substantially greater statistical confidence in the resulting calculation of change in anisocoria compared to results obtained using monocular measurements.

Pupillometers in accordance with the invention may additionally be used in the measurement of pupillary near-reflex, i.e. the constriction of the pupil which occurs as the point of fixation is brought closer to the eyes. Since the optical axis of the eye changes between near and far vision, study of the centre position of the pupil as pupillary near-reflex occurs provides information which is highly valuable in clinical interventions such as laser surgery for presbyopia.

Conventionally pupillary near-reflex is elicited by using a distant (>6 m) steady target as a fixation point, the pupil sizes for one or both eyes being measured for a few seconds. The target is then moved very close to the subject (e.g. <30 cm) and pupil size data are recorded during and after this manoeuvre.

Binocular pupillometric apparatus of the invention as hereinbefore defined may be adapted to measure pupillary near-reflex by incorporation of a visible fixation point which is moveable between near and far positions and which in use is viewable through the eyepieces by way of an accommodation lens positioned between the eyepieces and the near position of the fixation point, the focal length of the lens exceeding its distance from the far position of the fixation point whereby changes in distance between the observed virtual positions in respect of the fixation point at its near and far positions exceed the actual change in distance between these positions.

The moveable fixation point should operate so as to elicit pupillary near-reflex (i.e. accomodation reflex) without bringing about the pupil-light reflex. The background illumination should accordingly be substantially larger and brighter than the moveable fixation point; this point may therefore, for example, be a small and dimly illuminated light-emitting diode.

As described in greater detail hereinafter with regard to the accompanying drawings, it is readily possible in this way to provide a self-contained bench-top pupillometer unit which permits variation in the observed virtual position of the fixation point from a near position distance of about 25 mm to a far position distance of about 9.9 m.

This principle may equally be applied to other types of pupillometric apparatus, whether monocular or binocular (e.g. as described in WO-A-9407406), and such apparatus operable in this way constitutes a further feature of the invention. Thus according to this aspect of the invention there is provided pupillometric apparatus for assessing pupillary near-reflex in respect of at least one eye of a subject, said apparatus comprising an eyepiece for positioning against the said eye, sensing illumination means whereby in use the eye may be illuminated to generate images defining the pupil thereof, detector means permitting generation of pupil dimension data from the said images, and background illumination means serving in use to provide background illumination to the said eye, characterized in that the said apparatus further comprises a visible fixation point which is moveable between near and far positions and which in use is viewable through the eyepiece by way of an accommodation lens positioned between the eyepiece and the near position of the fixation point, the focal length of the said lens exceeding its distance from the far position of the fixation point whereby changes in distance between observed virtual positions in respect of the fixation point at its near and far positions exceed the actual change in distance between these positions.

Apparatus in accordance with this embodiment of the invention is preferably operable binocularly. In such binocular apparatus it is possible to provide a single moveable fixation point, which in general will be moveable along a longitudinal central axis of the apparatus, and which is viewable through the left and right eyepieces by way of a, single accomodation lens. This use of a single fixation point viewable by both eyes may encourage convergence and so simulate natural viewing conditions.

It is possible, however, that aberrations may occur in such apparatus, since a significant proportion of the light rays reaching the eyes of the subject may have travelled through parts of the accomodation lens which are at some distance from its central axis. It may therefore be preferable to use a system in which separate left and right moveable fixation points are viewable through the left and right eyepieces respectively by way of separate left and right accomodation lenses. Each fixation point in this system will in general be moveable along the central optical axis of the associated accomodation lens, and the two points will typically be linked together so as to be moveable in parallel. In this embodiment the two fixation point images will be merged by the subject's convergence reflex, the vergence effort required reducing as the image distance increases.

In order accurately to determine changes in the centre position of the pupil as accomodation changes between near and far fields, it is desirable that the pupil centre coordinates should be measured relative to a fixed point of the eye. Apparatus as described above for measurement of pupillary near reflex data therefore preferably incorporates processing software which is adapted to recognize biological pattens associated with the iris, in particular artefacts on the sclerocorneal limbus, which are well known to remain fixed despite changes in pupillary size.

In general the optical train required to project the pupil-defining images onto the image sensor of binocular pupillometers according to the invention is preferably as simple as possible, and typically may comprise a combining prism or series of mirrors followed by an objective lens, e.g. as described in greater detail hereinafter.

In the accompanying drawings, which serve to illustrate the invention without in any way limiting the same.

Figure 1:
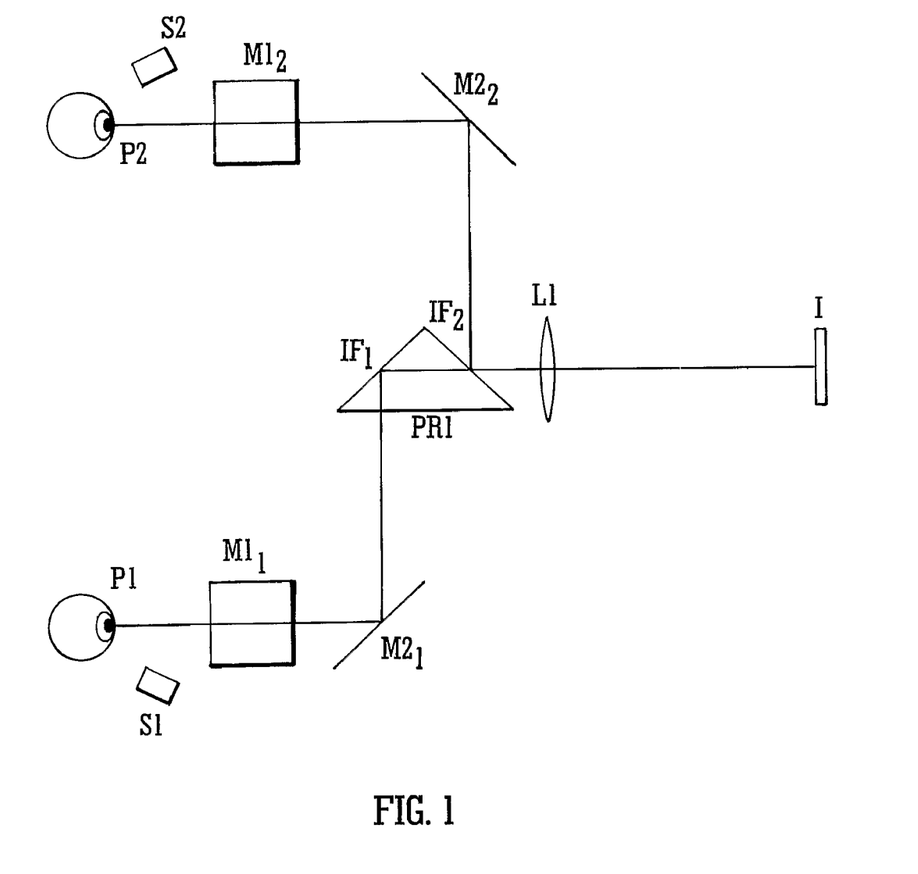
FIG. 1 is a schematic representation of the basic optical configuration of one embodiment of a pupillometer according to the invention.

Referring to FIG. 1 in more detail, combining prism PR1 causes images in respect of right and left pupils P1 and P2 to be projected onto image sensor 1 by way of objective lens L1. Total internal reflection occurs at interface IF1, the slanted face of the prism facing the optical pathway for pupil P1, and a surface reflection occurs at interface IF2, the slanted face of the prism facing the optical pathway for pupil P2.

Periscopes respectively comprising mirrors M$1_1$ and M$2_1$ and mirrors M$1_2$ and M$2_2$ are provided on the right and left channels and are rotatable about the central optical axes of M$2_1$ and M$2_2$ to allow adjustment for interpupillary distance. The eyes are independently illuminable by sets of infrared-emitting diodes S1 and S2.

In a representative embodiment objective lens L1 has a focal length of 50 mm, the distances of P1 to L1 and P2 to L1 are 150 mm and the distance L1 to I is 75 mm, giving a magnification of 0.5. It should be noted that the additional length of glass between IF1 and IF2 results in a slightly foreshortened effective overall optical path for P1 to I compared with P2 to I; the distance P1 to IF1 may be slightly lengthened compared with the distance P2 to IF2 in order to compensate for this. The image sensor I may, for example, be a ½ inch CCD sensor such as a Pulnix TM6B sensor.

Figure 2:
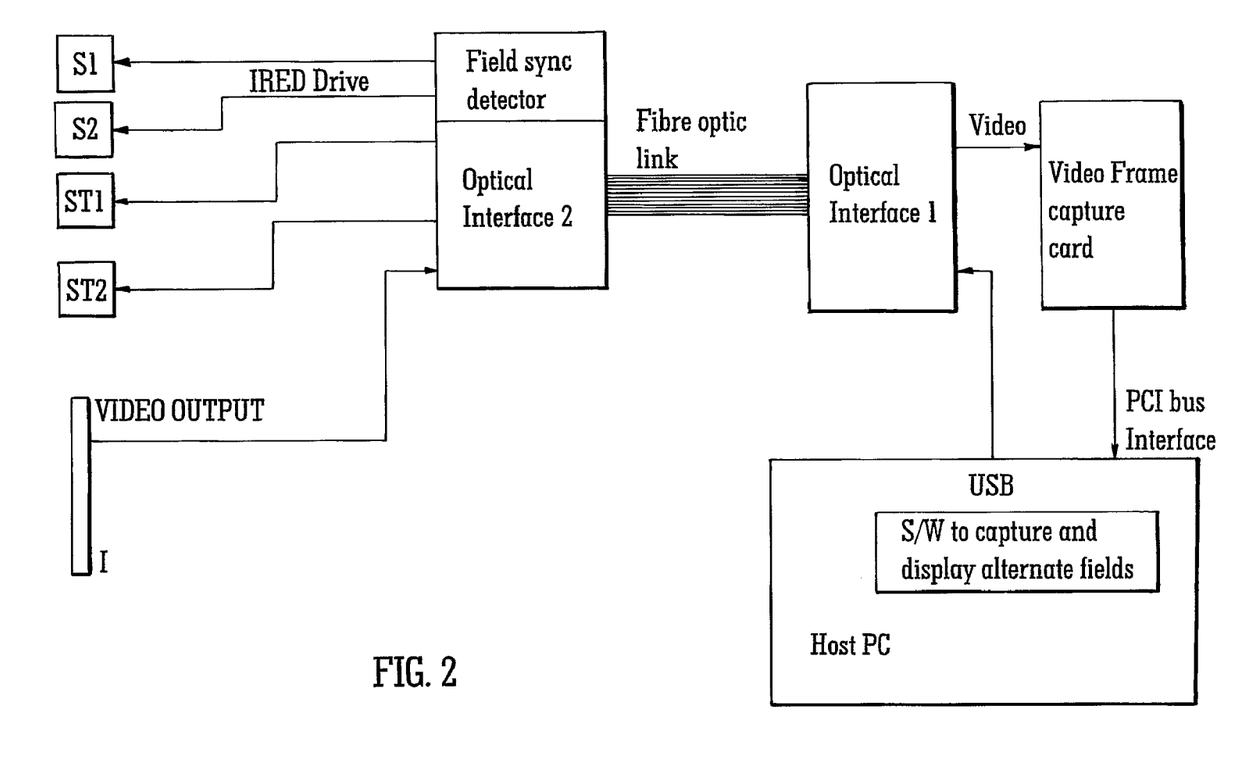
FIG. 2 is a block diagram of such a pupillometer and associated equipment.

As shown in FIG. 2, the infrared-emitting diode sets S1 and S2 are controlled via the infrared (IRED) drive by the field synchronization detector, which is triggered by the field scan synchronization pulses from the image sensor drive circuit incorporated in optical interface 2. The eyepieces may optionally also respectively incorporate stimulus lamps ST1 and ST2 (not shown in FIG. 1). These stimulus lamps may, for example, be light-emitting diodes, the intensity of which may be controlled by a digital-to-analogue converter incorporated in optical interface 2 and receiving input from software in the host personal computer PC.

The optical instrumentation may, for example, be contained in an steel frame covered with a moulded plastic skin. The periscopic eyepieces are preferably provided with rubber eyecups such as are used in ophthalmic equipment. The apparatus may be in portable form, e.g. having a housing with dimensions comparable to conventional binoculars, or may be a desktop unit, e.g. if this is preferred for extra stability.

The host personal computer, which incorporates software to capture and display the alternate fields in respect of left and right pupil images, may be a laptop model, e.g. using a PCM-CIA frame capture card, or a desktop model. It may be isolated from the pupillometer by an optical interface, as shown by the fibre optic link and optical interface 1 in FIG. 2, e.g. to aid compliance with medical device directive standards. Alternatively a small embedded computer may be incorporated into the same housing as the pupillometer and this optical interface may be omitted.

Figure 3:
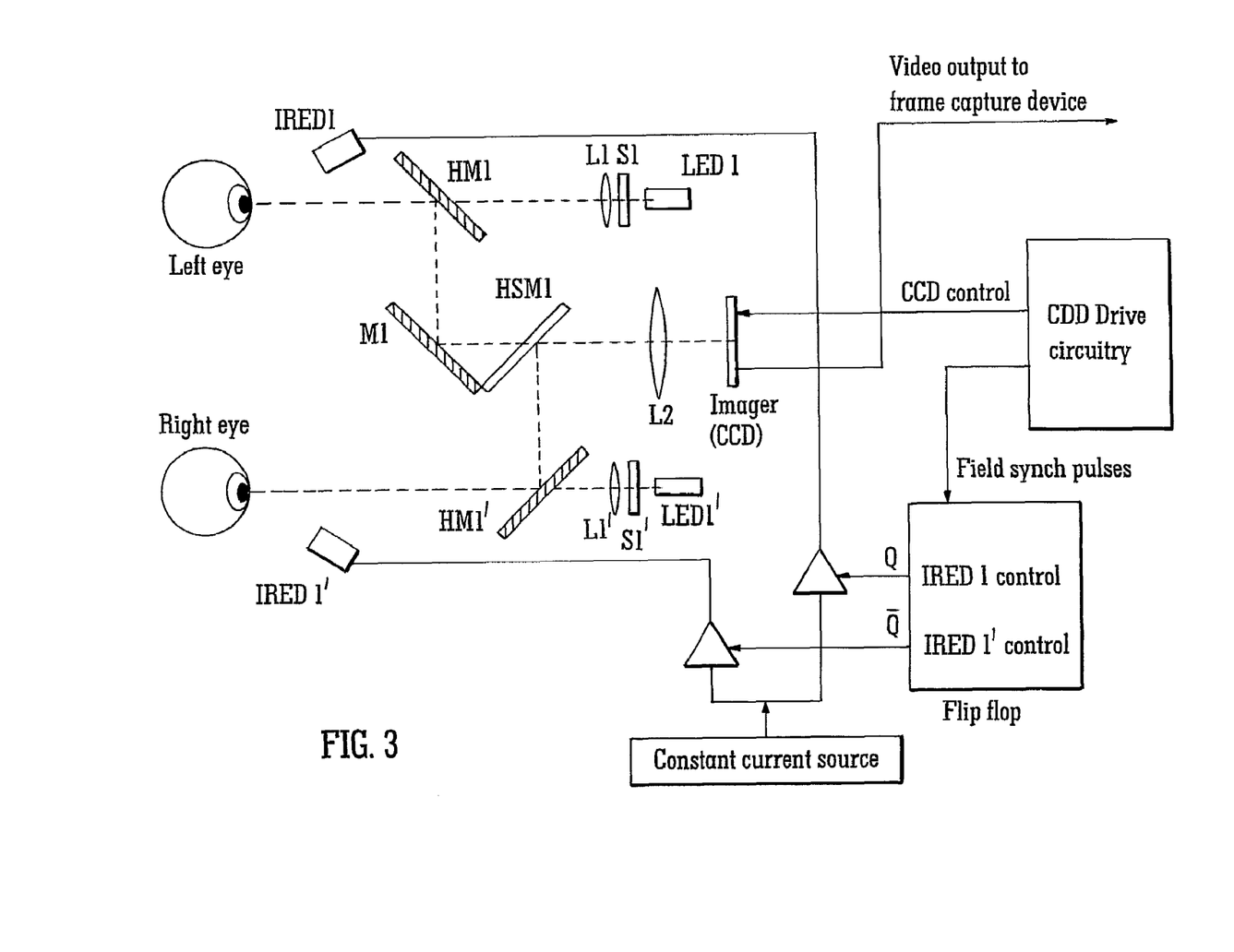
FIG. 3 is a schematic representation of the basic optical configuration of a second embodiment of a pupillometer according to the invention.

In the embodiment shown in FIG. 3, background visible light from light-emitting diodes LED1 and LED1' is transmitted through the hot mirrors HM1 and HM1' to each eye to illuminate the retinas. When field scan N is initiated by the CCD controller, output Q from the bistable flipflop becomes active and sensing infrared light from the infrared-emitting diode IRED1 irradiates the left eye and is then scattered by its iris. This infrared light is then reflected from the hot mirror HM1 onto the fully silvered mirror M1 and transmitted through half-silvered mirror HSM1, losing approximately 50% of its intensity in so doing. Lens L2 then forms an image of the iris and pupil of the left eye, covering its complete field of view. When field scan N is complete scan N+1 is initiated and output Q of the bistable flipflop becomes inactive whilst $\bar{Q}$ becomes active and sensing infrared light from infrared-emitting diode IRED1' is reflected from the right eye. This is then reflected off hot mirror HM1' and onto the CCD via the half-silvered mirror HSM1 and the objective lens L2, again losing approximately 50% of its intensity in so doing. Each time the entire active area of the CCD imager is covered by a single iris and pupil image.

The eyepieces for the left and right eyes are each illuminated by their own dedicated illumination system, respectively comprising light-emitting diode LED1 or LED1', lens L1 or L1' and screen S1 or S1'. These systems are controlled by dedicated hardware which allows accurate adjustment of the drive currents to LED1 and LED1', permitting precise manual or automated calibration of the illumination level output from each system.

Figure 4:
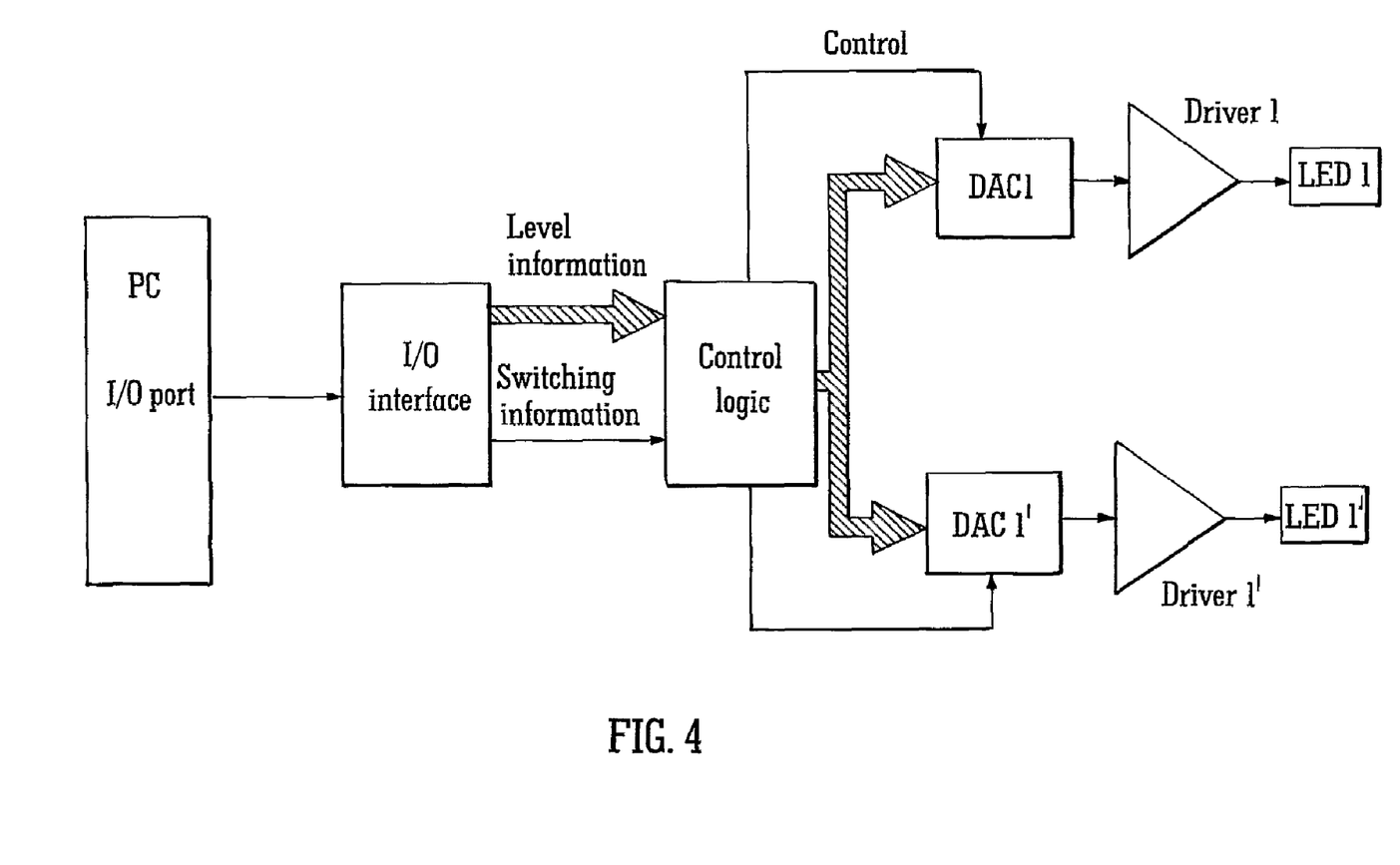
FIG. 4 is a block diagram of such a pupillometer and associated equipment.

As shown in FIG. 4, switching and adjustment of the illumination levels may be controlled from the output ports of a host personal computer dedicated to the pupillometer for image processing. The I/O port supplies all switching and level information to the control logic and digital to analogue converters DAC1 and DAC1' in the pupillometer, with the precise level and timing of the switching of the illuminating light emitting diodes LED1 and LED1' being controllable entirely by software.

Figure 5:
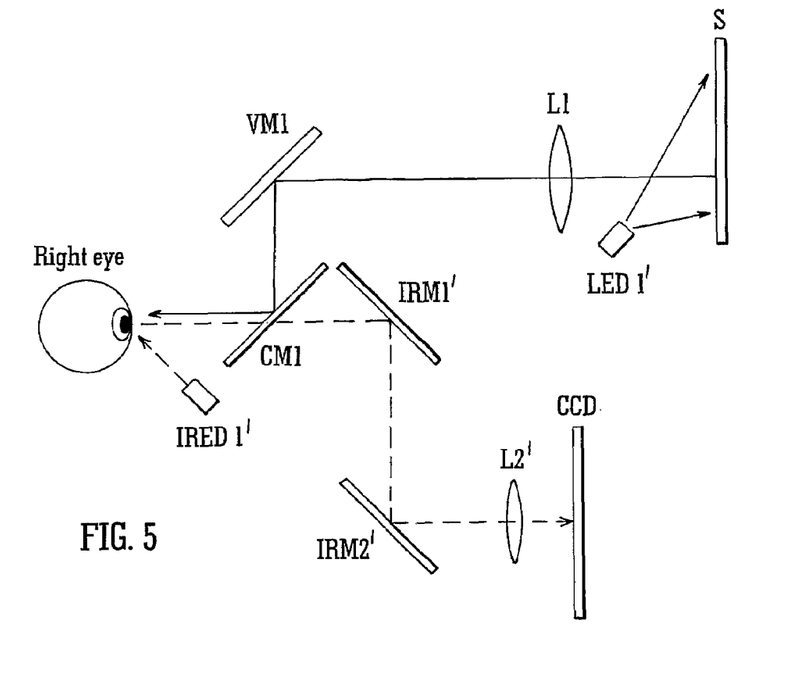
FIG. 5 is a schematic side elevation of a further embodiment of a pupillometer according to the invention showing an alternative optical train providing vertical separation of the infrared sensing irradiation and the background visible illumination.

In the embodiment shown in FIG. 5, sensing infrared light from infrared-emitting diode IRED1' is scattered from the iris of the right eye, passes through cold mirror CM1, is reflected by first-surface infrared mirrors IRM1' and IRM2' and is focussed by lens L2' onto the CCD imager. Sensing infrared light from infrared-emitting diode IRED1 (not shown) similarly scatters from the iris of the left eye (not shown), passing through cold mirror CM1 to first-surface infrared mirrors IRM1 and IRM2 (not shown) and lens L2 (not shown) to the CCD imager. A control system as described above is used to generate and record data in respect of alternate left and right pupil images.

Screen S is illuminated by left and right light-emitting diodes LED1 (not shown) and LED1', which are positioned so as to be outside the field of view of the subject. Visible background light from screen S is transmitted through lens L1 and reflected by visible mirror VM1 and cold mirror CM1 to both the left and right eyes.

Figure 6:
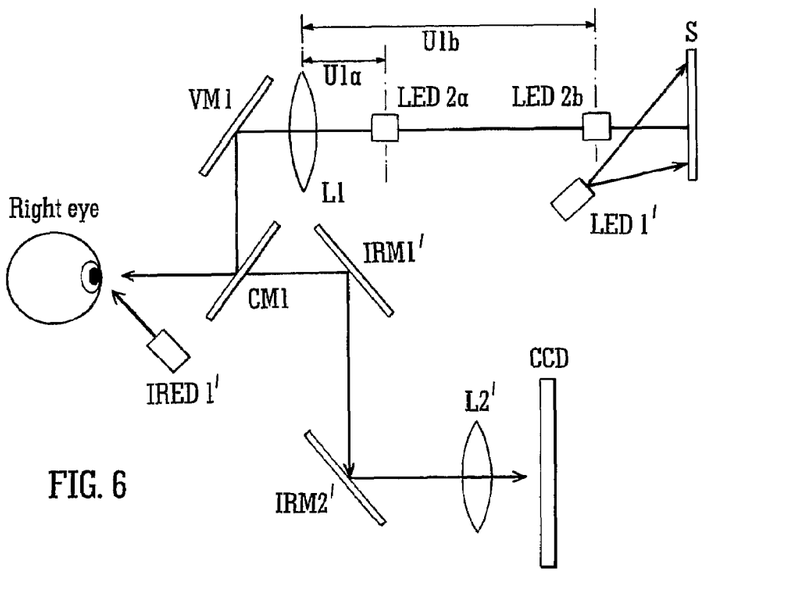
FIG. 6 is a schematic side elevation of a similar embodiment to that of FIG. 5, modified to incorporate a movable fixation point.
Figure 7:
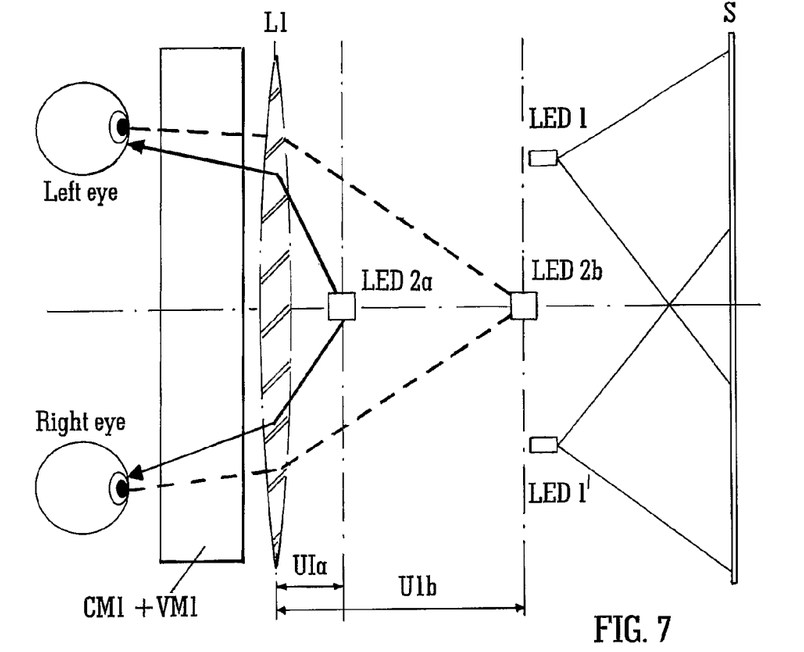
FIG. 7 is a schematic view from above of the visible light optical system for the embodiment of FIG. 6.

The embodiment shown in FIGS. 6 and 7 further incorporates a moveable fixation point comprising a light-emitting diode moveable between near and far positions shown as LED2a and LED2b respectively. The fixation point may be moved by means of a simple slider or, if detailed timing data regarding its movement is required, by means of an electromechanical device such as a solenoid or stepping motor. The light emitting diode LED2 is chosen to be small and dimly lit compared to the background illumination from screen S so that changes in its position will not elicit pupillary-light reflexes in subjects; in the illustrated embodiment the background illumination area subtends angles of more than 30° horizontally and 16° vertically.

The focal length of accommodation lens L1 is greater than both U1a and U1b, the distances between L1 and the near and far fixation point positions LED2a and LED2b. Subjects will therefore at all times view virtual images of LED2 which are upright and magnified. The apparent position of LED2 as it is moved between the near and far positions LED2a and LED2b will depend on the focal length of L1. For an arrangement intended to fit within a small bench-top pupillometer unit, a convenient focal length for L1 is 100 mm. Then, if U1a and U1b are respectively 20 mm and 99 mm, the apparent distance of the fixation point (i.e. the virtual image distance in respect of LED2) can be varied within the range 25 mm to 9.9 m.

It will be appreciated that since the field stop of the visible light optical system is the boundary of accommodation lens L1, this lens needs to be at least as wide as the widest inter-pupillary distance expected to be encountered in a subject (variations in inter-pupillary distances preferably being accommodated by the use of periscopic eyepieces as described above in respect of other embodiments of the invention). In practice the lens should have some (e.g. 5-10%) additional width to minimize distortions which occur when viewing takes place through the edges of a lens.

Figure 8:
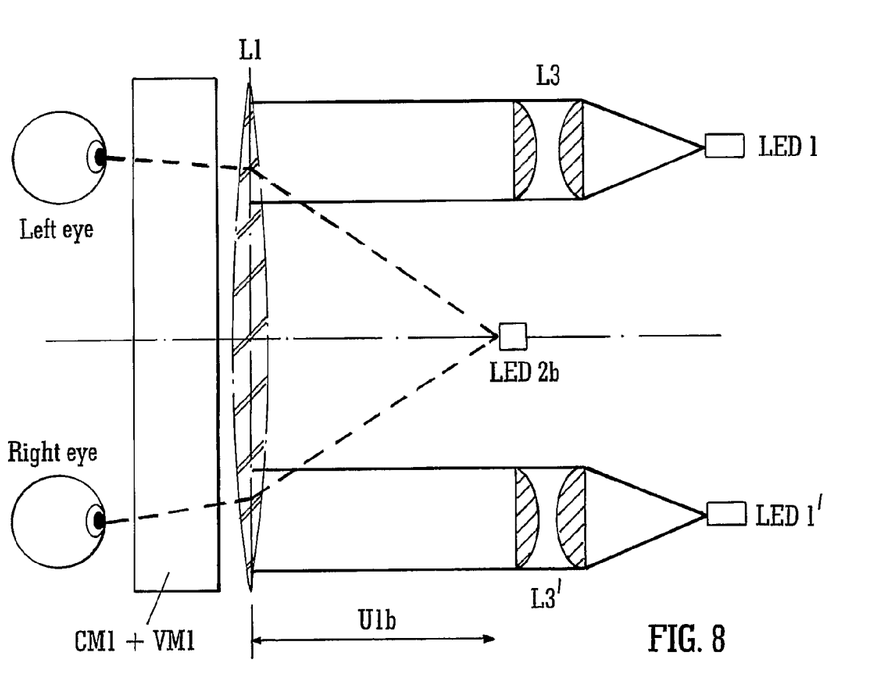
FIG. 8 is a schematic view from above of an alternative visible light optical system incorporating a moveable fixation point.

In the embodiment of FIG. 8, collimating lens systems L3 and L3' are used to illuminate the left and right eyes with highly collimated beams of background visible light emanating from light-emitting diodes LED1 and LED1' respectively. In this way separately controllable (and, if desired, alternating) visible light stimulation may be provided to the subject's eyes. Because the beams are highly collimated there is no crosstalk between them, i.e. the left eye will see only the left eye stimulus and the right eye will see only the right eye stimulus. This permits highly effective unilateral stimulation of each eye, for example as is required when measuring relative afferent pupillary defect.

When measuring pupillary near-reflex, the optical train of the apparatus of FIG. 8 should preferably be such that the image of the moveable fixation point when at its far position appears essentially at infinity, in order to ensure that the lines of sight of the two eyes are parallel and not converging. It is possible, however, to adapt the apparatus to allow for reduced far position image distances (i.e. such that the eyes are somewhat convergent) by repositioning the two collimated light beam sources to ensure that each is directed at only one eye. This may, for example, be achieved by directing the left collimated light source onto the right eye and the right collimated light source onto the left eye. It will be appreciated that, as a generality, the area of illumination provided by each collimated light source should be wide enough to cover the appropriate eye regardless of variations in interpupillary distances between different subjects, without being so wide as to induce crosstalk.

Figure 9:
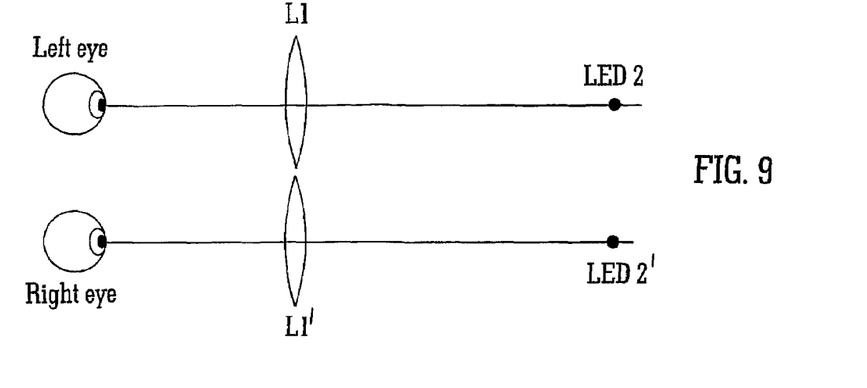
FIG. 9 is a partial schematic view from above of a system incorporating two moveable fixation points and two accomodation lenses.

FIG. 9 is a partial schematic representation of an alternative embodiment in which separate fixation points LED2 and LED2' are respectively moveable along the central optical axes of accomodation lenses L1 and L1', and are respectively viewable by the left and right eyes of the subject; for simplicity the remainder of the optical train is not shown.

It will be appreciated that lenses L1 and L1' should have identical sizes and optical properties. Their diameters should preferably be such that they accomodate variations in inter-pupillary distances between different subjects. These distances generally vary between about 55 mm and 75 mm in human subjects, so that the use of accomodation lenses with diameters of about 65 mm should in general give consistent results in this respect.

Figure 10:
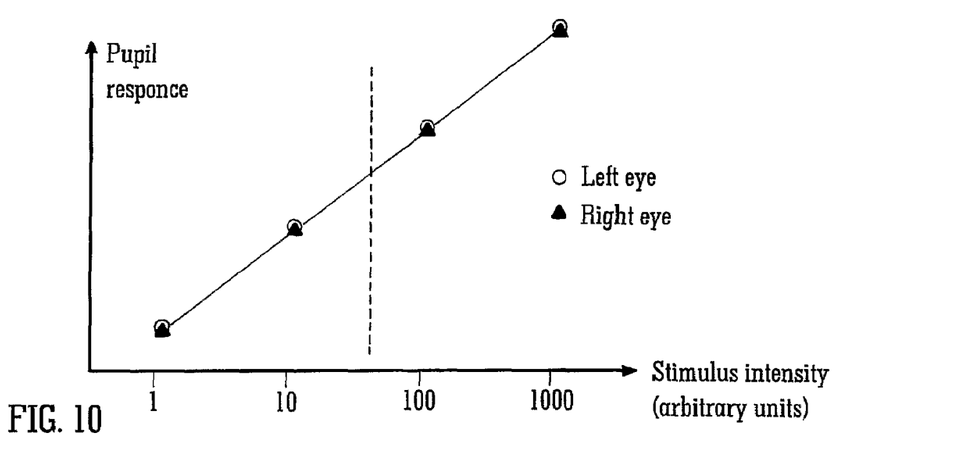
FIG. 10 is a pupillary response profile in respect of a subject with no relative afferent pupillary defect.

FIG. 10 shows, left and right pupillary response profiles in a case where each eye has been stimulated with pulses of four different intensities, increasing by a factor of ten each time, thereby giving a log-linear plot covering three decades of stimulus intensity. The profiles overlap, indicating an absence of relative afferent pupillary defect in the subject. The vertical dotted line shows the approximate effect of the equivalent swinging flashlight test carried at only a single stimulus intensity, with no significant difference in response being seen between left and right eye stimuli.

Figure 11:
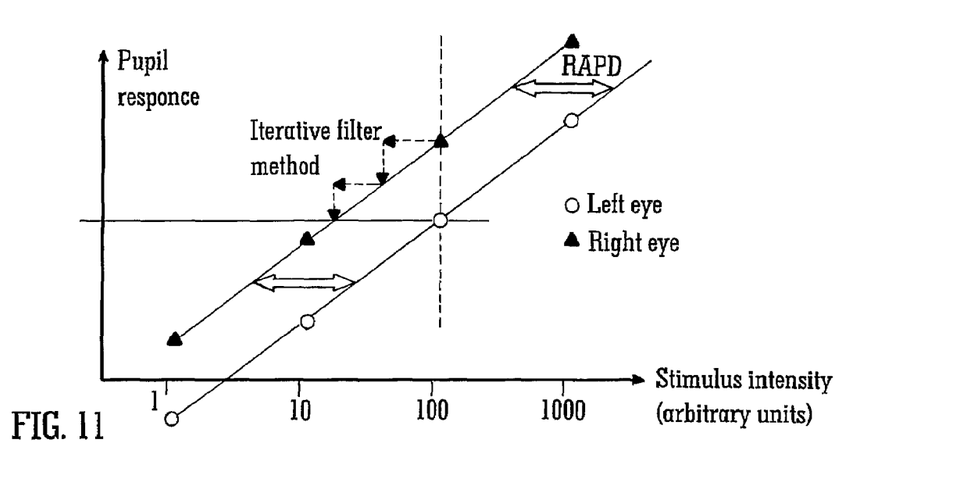
FIG. 11 is a pupillary response profile in respect of a subject with relative afferent pupillary defect.

FIG. 11 shows the corresponding profiles for a subject with relative afferent pupillary defect of the left eye. At all light levels the pupillary response when the left eye is stimulated is lower than the response when the right eye is stimulated. The amount of relative afferent pupillary defect may be determined by calculating the horizontal shift between the two profiles, as indicated by the horizontal arrows. The dotted lines show how this value would be determined using the swinging flashlight test, where filters are used iteratively to attenuate one stimulus in order to bring together the pupillary responses to the two stimuli. The greatly enhanced intensity range used in accordance with the invention is readily apparent

The invention claimed is:

1. A pupillometric apparatus for assessing pupillary near reflex in respect of at least one eye of a subject, the apparatus comprising an eyepiece for positioning against the eye, sensing illumination means whereby in use the eye may be illuminated to generate images defining the pupil thereof, detector means permitting generation of pupil dimension data from the images, and background illumination means serving in use to provide background illumination to the eye, wherein the apparatus further comprises a visible fixation point which is moveable between near and far positions and which in use is viewable through the eyepiece by way of an accommodation lens positioned between the eyepiece and the near position of the fixation point, the focal length of the lens exceeding its distance from the far position of the fixation point whereby the distance between observed virtual positions in respect of the fixation point at its near and far positions exceeds the actual distance between these positions.

2. The apparatus of claim 1, which is operable binocularly through left and right eyepieces.

3. The apparatus of claim 2, wherein a single moveable fixation point is viewable through the binocular eyepieces by way of a single accomodation lens.

4. The apparatus of claim 3, wherein the moveable fixation point comprises a light-emitting diode having small size and low operating intensity compared to the background illumination, such that in use it does not elicit a pupillary-light reflex upon movement of the fixation point.

5. The apparatus of claim 2, wherein separate left and right moveable fixation points are viewable through the left and right eyepieces respectively by way of separate left and right accomodation lenses.

6. The apparatus of claim 5, wherein the moveable fixation point comprises a light-emitting diode having small size and low operating intensity compared to the background illumination, such that in use it does not elicit a pupillary-light reflex upon movement of the fixation point.

7. The apparatus of claim 2, wherein (i) the sensing illumination means are such that in use the left and right eyes are independently and alternately illuminated via the eyepieces to generate alternating images respectively defining the pupils of the left and right eyes, (ii) the detector means comprise an optical train and single image sensor configured such that in use the alternating left and right pupil images are transmitted to the same part of the sensor, and (iii) the apparatus further includes signal processing means associated with the sensor and adapted to separate signals generated therein by the alternating images and to generate separated image data representative of the dimensions of the left and right pupils.

8. The apparatus of claim 7, wherein the sensing illumination means comprise infrared-emitting diodes respectively associated with the left and right eyepieces.

9. The apparatus of claim 8, wherein the single image sensor is a two-dimensional charge-coupled device array.

10. The apparatus of claim 9, wherein field synchronization pulses from the charge-coupled device array are used to trigger the alternate illumination of the left and right eyes.

11. The apparatus of claim 7, wherein the single image sensor is a two-dimensional charge-coupled device array.

12. The apparatus of claim 11, wherein field synchronization pulses from the charge-coupled device array are used to trigger the alternate illumination of the left and right eyes.

13. The apparatus of claim 1, which incorporates imaging processing software adapted in use to recognize artefacts on the sclerocorneal limbus in order to provide a fixed reference point for the pupil dimension data.

14. The apparatus of claim 1, wherein the background illumination means comprise one or more light-emitting diodes.

15. The apparatus of claim 14, wherein the background illumination means comprise light-emitting diodes adapted to illuminate the left and right eyepieces independently.

16. A binocular apparatus for substantially simultaneous determination of pupil dimensions in respect of the left and right eyes of a subject, the apparatus comprising (i) left and right eyepieces for positioning against the eyes, (ii) sensing illumination means whereby in use the left and right eyes are independently and alternately illuminated via the eyepieces to generate alternating images defining the left and right pupils, (iii) an optical train whereby in use the alternating left and right pupil images are transmitted to the same part of a single image sensor, and (iv) signal processing means associated with the sensor and adapted to separate signals generated therein by the alternating images and to generate separated image data representative of the dimensions of the left and right pupils.

17. A method for substantially simultaneous determination of pupil dimensions in respect of the left and right eyes of a subject, the method comprising alternately illuminating the left and right eyes in order to generate alternating images defining the left and right pupils, projecting the alternating left and right pupil images onto the same part of a single image sensor, separating signals generated by the sensor in respect of left pupil images and right pupil images, and generating separated image data representative of the dimensions of the left and right pupils.

18. The method of claim 17, wherein the eyes are additionally controllably illuminated with background visible light.

19. The method of claim 18, wherein the background illumination to each eye is independently controllable.

20. The method of claim 19, wherein the independently controllable background illumination is used to apply stimulating light pulses of controlled duration and controlled varying intensities to each eye in turn to permit generation of separate profiles of pupillary response against stimulating light intensity for the left and right eyes.

21. The method of claim 19, wherein the background illumination is switched off to test pupillary response to darkness.

22. The method of claim 18, wherein the background illumination is switched off to test pupillary response to darkness.

23. The method of claim 17, wherein anisocoria between the left and right eyes is determined.

24. The method of claim 23, wherein the anisocoria is pharmaceutically induced.

* * * * *